(12) United States Patent
Carbone et al.

(10) Patent No.: US 9,364,830 B2
(45) Date of Patent: Jun. 14, 2016

(54) FUNCTIONALIZED MICROFLUIDIC DEVICE FOR IMMUNOFLUORESCENCE

(75) Inventors: Roberta Carbone, Milan (IT); Emanuele Barborini, Milan (IT); Dario Bandiera, Milan (IT)

(73) Assignee: Tethis S.R.L., Milan (IT)

( * ) Notice: Subject to any disclaimer, the term of this patent is extended or adjusted under 35 U.S.C. 154(b) by 0 days.

(21) Appl. No.: 13/146,113

(22) PCT Filed: Jan. 26, 2010

(86) PCT No.: PCT/EP2010/050820
§ 371 (c)(1),
(2), (4) Date: Jul. 25, 2011

(87) PCT Pub. No.: WO2010/084196
PCT Pub. Date: Jul. 29, 2010

(65) Prior Publication Data
US 2011/0281267 A1    Nov. 17, 2011

(30) Foreign Application Priority Data

Jan. 26, 2009  (EP) .................. PCT/EP2009/000465

(51) Int. Cl.

| | | |
|---|---|---|
| C12M 1/00 | (2006.01) | |
| G01N 33/567 | (2006.01) | |
| G01N 33/574 | (2006.01) | |
| C12P 21/04 | (2006.01) | |
| G01N 15/06 | (2006.01) | |
| B01J 8/00 | (2006.01) | |
| B01L 3/00 | (2006.01) | |
| B82Y 30/00 | (2011.01) | |
| G01N 33/53 | (2006.01) | |
| G01N 33/551 | (2006.01) | |
| B01J 19/00 | (2006.01) | |
| C12Q 1/68 | (2006.01) | |
| G01N 33/543 | (2006.01) | |
| G01N 33/553 | (2006.01) | |

(52) U.S. Cl.
CPC ........... *B01L 3/5027* (2013.01); *B01J 19/0093* (2013.01); *B82Y 30/00* (2013.01); *C12Q 1/68* (2013.01); *C12Q 1/6841* (2013.01); *G01N 33/5304* (2013.01); *G01N 33/543* (2013.01); *G01N 33/551* (2013.01); *B01J 2219/00605* (2013.01); *B01L 2300/0636* (2013.01); *B01L 2300/0822* (2013.01); *B01L 2300/0887* (2013.01); *G01N 33/54346* (2013.01); *G01N 33/553* (2013.01); *G01N 2333/726* (2013.01)

(58) Field of Classification Search
USPC .................. 435/6.1, 7.23, 70.3, 283.1, 287.7; 422/68.1, 603; 977/700, 773
See application file for complete search history.

(56) References Cited

U.S. PATENT DOCUMENTS

| | | | |
|---|---|---|---|
| 6,613,560 B1 | 9/2003 | Tso et al. | |
| 7,189,367 B2* | 3/2007 | Yamamoto et al. | ............ 422/130 |
| 2002/0076825 A1* | 6/2002 | Cheng | ............... B01L 3/502761 |
| | | | 436/174 |
| 2009/0005238 A1* | 1/2009 | Falaras | .......................... 502/200 |

FOREIGN PATENT DOCUMENTS

| | | |
|---|---|---|
| WO | 02/066685 A1 | 8/2002 |
| WO | 2004011672 A1 | 2/2004 |
| WO | 2004067444 A1 | 8/2004 |
| WO | 2007009994 A1 | 1/2007 |
| WO | 2007/082302 A1 | 7/2007 |

OTHER PUBLICATIONS

Carbone et al, Biocompatibility of cluster-assembled nanostructured TiO2 with primary and cancer cells, 2006, Biomaterials 27, 3221-3229.*
Kenausis et al, Poly(L-lysine)-g-Poly(ethylene glycol) Layers on Metal Oxide Surfaces: Attachment Mechanism and Effects of Polymer Architecture on Resistance to Protein Adsorption, J. Phys. Chem. B 2000, 104, 3298-3309.*
Nagai et al, Flexible manipulation of microfluids using optically regulated adsorption/desorption of hydrophobic materials, 2007, Biosensors and Bioelectronics 22, 1968-1973.*
Data sheet Sylgard 184—Silicone Elastomer, 2014, Downloaded from the internet [www.dowcorning.com/DataFiles/090276fe80190b08] printed on Apr. 17, 2015, pp. 1-4.*
Kommireddy et al, Layer by layer assembly of TiO2 nanopraticles for stable hydrophilic biocompatible coatings, 2005, Journal of Nanoscience and Nanotechnology, 5, 1081-1087.*
Lynda J. Campbell, "Cytogentic and Fish Techniques in Myeloid Malignancies," Methods in Molecular Medicine, Myeloid Leukemia: Methods and Protocols, 2006, pp. 13-26, vol. 125, Humana Press Inc., Totowa, NJ.
V.J. Sieben, et al., "Fish and chips: chromosomal analysis on microfluidic platforms," IET Nanobiotechnol., 2007, pp. 27-35, vol. 1, No. 3, The Institution of Engineering and Technology.
Xuan Huang et al., "Enforced Adhesion of Hematopoietic Cells to Culture Dish Induces Endomitosis and Polyploidy," Introduction of Polyploidy of L1210 Cells, Cell Cycle, 2005, pp. 801-805, vol. 4, Issue 6, Landes Bioscience.
Teruo Fujii, PDMS-based microfluidic devices for biomedical applications, Microelectronic Engineering, vol. 61-62, Elsevier Publishers BV., Amsterdam, Jul. 1, 2002, pp. 907-914.
International Search Report and Written Opinion for corresponding International Application No. PCT/EP2010/050820, dated Jun. 22, 2010 (14 pages).

* cited by examiner

*Primary Examiner* — Narayan Bhat
(74) *Attorney, Agent, or Firm* — McCormick, Paulding & Huber LLP (57) ABSTRACT

It is described a microfluidic device, for use in the field of analytical fluorescence based assays and, in particular, in FISH assays.

14 Claims, 10 Drawing Sheets

FUNCTIONALIZED MICROFLUIDIC DEVICE FOR IMMUNOFLUORESCENCE

CROSS REFERENCE TO RELATED APPLICATIONS

This application is entitled to the benefit of and incorporates by reference essential subject matter disclosed in International Patent Application No. PCT/EP2010/050820 filed on Jan. 26, 2010 and International Patent Application No. PCT/EP2009/000465 filed on Jan. 26, 2009.

FIELD OF THE INVENTION

The present invention relates to the field of analytical fluorescence based assays and, in particular, to a device which may be used in FISH assays. A method for efficiently performing said test by the use of the device of the invention is encompassed as well.

BACKGROUND ART

Microfluidics is a recent multidisciplinary science, which deals with very small volumes of liquids, from microliters down to femtoliters. Its earliest application concerned inkjet printheads, but it proved to be suitable for the development of "lab-on-a-chip" technology, especially in the field of biotechnology, wherein samples are characterized by very small sizes. Molecular biology, enzymatic analysis, genomic analysis, proteomics, clinical pathology, diagnostics, environmental analysis, etc. all are fields of potential exploitation of microfluidics.

At such microscale dimensions, fluids may show a very different behavior compared to macroscale, a feature which must be taken into account when designing microfluidic devices or experiments which make use of them. For instance, surface tension, energy dissipation, fluidic resistance and diffusion, may largely influence the outcome of the experiments.

For these reasons, ordinary or customary protocols of these assays cannot be directly used in microfluidic devices, but special procedures must be instead designed before implementation.

Advantages linked to the use of microfluidics go back to the easier handling allowed by such devices, the higher flux control permitted, the reduced time of analysis, the high control granted over both concentration and molecular interactions, the incomparable cost saving for reagents and waste products, thus making its use more environmental friendly and giving the ability to process more samples with less space due to reduced instruments hindrance.

The above advantages enable experiments including the use of microfluidic devices to be automated, which would be very interesting from the industrial point of view.

Microchip biotechnology, in particular, is gaining the most from microfluidics, thanks to new developed integrated workflow.

Lab-on-chip devices are few square millimeters to few square centimeters chips on which the bio-assays are reproduced at much smaller scale, in the form of microfluidic circuits.

Lab-on-chip devices, or microfluidic circuits for use in said devices, are widely described in the literature.

U.S. Pat. No. 6,613,560 discloses miniaturized devices for conducting chemical and biochemical processes, in particular a microreactor for conducting DNA amplification; this document faces the problem of unwanted adsorption of the sample under analysis by the walls of the microreactor, and proposes the use of microreactors made (or with surfaces covered) with materials that exhibit reduced adsorption of compounds present in the sample.

International patent application WO 95/22051 discloses a flow cell device having in its channels immobilized reagents which produce an electrically or optically detectable response to an analyte which may be contained in a test sample.

European patent application EP 1542010 discloses a microfluidic device comprising a reaction area, designed to host a reaction between at least a species present in the sample and at least one specific substance, fixed in the area, that can cause interaction specifically or non-specifically with one or more predetermined substances (target species). The secure fixing of the specific substance to the walls of the microfluidic circuit is obtained by means of an intermediate, immobilized film (generally made of an organic compound) previously formed on said walls.

Lab-on-chip devices are already available for use in a variety of analytical techniques, such as electrophoresis, chromatography, staining, fluorescence cytometry, protein analysis, polymerase chain reaction, blood analysis, etc. and, as a further application, Fluorescence In Situ Hybridisation (FISH). As a general reference to FISH, see, for instance, "Cytogenetic and FISH techniques in Myeloid Malignancies", L. J. Campbell, Methods in Molecular Medicine, 2006, Vol. 125, pp. 13-26.

More in detail, FISH is a very sensitive tool used in diagnostics for the detection of genome alterations.

FISH represents a very promising diagnostic tool for the identification of chromosomal rearrangements or abnormalities, which cannot be detected with other conventional techniques. For example, the analysis of alterations in the chromosomes may be predictive of a future disease or of a therapy response.

As a first step, FISH requires the cell immobilization onto a support, such as, for instance, a microscope glass slide; after that, cells undergo a protein digestion in order to remove cytoplasmic and chromosomal proteins, thus allowing an improved "access" to chromosomal DNA, which needs to be denatured, for example by incubating with formaldehyde-based solutions. After cell dehydration with ethanol-based series of solutions, DNA probes are added. Denaturation is then performed at about 75° C. for 2-5 min and incubation is allowed. A treatment with a suitable post-hybridization solution enables non-specific disturbing bindings due to cross-hybridization to be avoided. Abnormality sites in the chromosome sequence become thus evident by fluorescence imaging.

Prior to FISH, the analysis of DNA made use of scarcely cost-effective methods, while, nowadays, FISH allows researchers to rapidly investigate and understand the basis of many diseases and cancers.

For instance, FISH finds already application in bone marrow testing for haematological tumors, such as leukaemia, lymphoma and myeloma, in solid tumor, lymph node and peripheral blood testing, in preimplantation genetic diagnosis, in prenatal and in postnatal genetic abnormalities screenings.

As a general advantage, FISH may be applied directly to tumor samples, such as biopsies, sections or paraffin-embedded material, providing resolution up to single cell level, enabling the detection of rare events on a suitable cell sample. Despite the potential advantages offered by this technique, its practical adoption has been hindered so far by several drawbacks.

In first place, FISH is extremely expensive, both in terms of reagent costs and of men-time and machine-time necessary to perform the protocol and the image analysis. This limit prevents FISH from being a mass screening method.

A suitable approach to overcome this limit would be the development of a miniaturized protocol by exploiting the features of microfluidic devices.

However a further limit of FISH protocols and devices that can be predicted is the low efficiency of cell adhesion in microfluidic devices; this is due to the fact that, owing to the very limited cross-sections of microfluidic channels, relatively high pressures must be applied to the liquid samples in order to have these moving in the device, which in turn lead to relatively high flow rates. For instance, the article "FISH and chips: chromosomal analysis on microfluidic platforms", V. J. Sieben et al, IET Nanobiotechnologies, 2007, 1 (3) pp. 27-35, describes a standard adhesion protocol by cytospinning, that however only obtains a yield of retention of the target analytes in the channel of the microfluidic device of 20%. This feature could increase the rate of "false negatives" when searching for rare alterations.

A microfluidic device capable of efficiently immobilizing cells, suitable to perform FISH assays, would help in spreading the use of the technique.

Several prior art documents have the task of improving the retention of analytes in the channels of microfluidic devices.

The paper "Enforced Adhesion of Hematopoietic Cells to Culture Dish Induces Endomitosis and Polyploidy", X. Huang et al., Cell Cycle, 4(6), pages 801-805, discloses the use of substrates functionalized with poly-D-lysine for enhancing cells adhesion; substrates with a poly-D-lysine coating, commercially available for instance from BD Biosciences, are presently considered the state-of-the-art for cells adhesion and are commonly used in this field of research.

International patent application WO 2008/031228, in the name of the University of Alberta, discloses a fixating protocol that allows to reach a percentage of adhered cells up to 75% of the total. The immobilization of cells in the microfluidic channels is obtained by raising the temperature in the range between 50 and 95° C. for a period of time, determined by intervention of a human operator, sufficient to allow immobilization of a portion of a population of cells of interest. As a consequence, despite the improvement in the percentage of adhered cells, the method of this document still suffers from the limits that the immobilization step must be controlled by a human operator, and that the relatively high temperatures needed in this step could damage some cells. Besides, the application describes two embodiments of microfluidic device, called "Microchip" and "Circulating Microchip", respectively. The embodiment named "Microchip" is made of a 0.5 mm thick microscope glass slide carrying the microfluidics and a coverslip 0.17 mm thick, declared to be necessary to create a minimum working distance for high resolution imaging. Both the device components are extremely fragile and require an extremely careful handling during assembling, preventing an easy scale up of the device in industrial settings. The embodiment named "Circulating Microchip" is made of two 1.1 mm thick microscope glass slides and of a middle PDMS layer 0.254 mm thick. This embodiment overcomes the fragility problems of "Microchip", but its thickness does not allow the use of a 100× lens for the image acquisition, thus preventing to obtain high resolution images, as required by current FISH standards.

European patent application EP 1215186 discloses a support, said to be useful for immobilizing oligonucleotides, that can be used in the fabrication of microfluidic devices; this support has the surface functionalized with an oxide chosen among $HfO_2$, $TiO_2$, $Ta_2O_5$, $ZrO_2$ and their mixtures, treated after their deposition in order to make their surface hydrophilic. This document is silent however about the immobilization of cells.

International patent application WO 00/33084 discloses a wide range of devices for use in diagnostics, in which the active surface is functionalized with organic compounds, possibly laid over a "gelled network" oxide. This document does not give any information about actual retention yields of cells.

Accordingly, a FISH device and method which would overcome the disadvantages of the prior-art methods, both classic and microfluidic, is needed.

In particular, it would be desirable to design a device and a process, which would be cheap, easy to handle, scale up and perform, fast to be carried out and efficient as well.

SUMMARY OF THE INVENTION

The present invention concerns an improved microfluidic device, which may be suitably and advantageously used in analytical fluorescence based techniques. A tailored protocol for using said device, which results in surprisingly and unexpected results, is disclosed as well.

The first object of the invention is a microfluidic device comprising at least a slide and a part in which a groove is present, said slide and part being such that by their joining a microchannel is formed, characterized in that at least the area on the surface of said slide facing said microchannel is functionalized with a nanostructured metal oxide preferably selected among Ti oxide, Zn oxide or Zr oxide.

A further object of the invention is the use of the device of the invention for performing analytical fluorescence based assays.

As a still further object, the present invention concerns a method for performing analytical fluorescence based assays using the microfluidic device of the invention.

DETAILED DESCRIPTION OF THE INVENTION

In a first aspect thereof, the invention concerns a microfluidic device. The device of the present invention finds applications in the field of analytical fluorescence based assays and, in particular, it may be used for performing FISH assays.

With respect to the known devices, the device here disclosed has several advantages, which will be appreciated by the skilled person in the art.

The improved microfluidic device of the present invention is formed by coupling at least a slide and a part in which a groove is present, so that the joining of these (at least) two elements defines a microchannel in the device. Although other configurations may be envisaged, the most common structure for these devices is the one in which the groove does not extend along the whole length of the part in which it is present, and the microchannel is accessed from the top surface of the device, via through holes formed in the part (and in other possible elements making up the complete device); the rest of the description will be made with reference to this common structure.

Within the present invention, any suitable slide may be used, for instance made of transparent materials such as glass, quartz or some plastics. Glass, in particular, is the preferred material for its chemical inertness, its transparency, its low cost, its poor porosity, its hydrophilicity and its long-lasting stability. For convenience, use can be made of a standard microscope slide, which is, preferably in the form of a thin sheet of glass, such as borosilicate, fused silica or even soda-lime, sizing about 25×76×1 mm.

The slide used within the present invention has at least the area, that in the complete device forms a wall of the microchannel, functionalized with a nanostructured metal oxide, in order to improve cell adhesion; in the following, nanostructured metal oxides will be referred to as ns-$MO_x$, in which M stands for a metal.

Among the ns-$MO_x$, the preferred ones are Zn oxide (ns-ZnO), Zr oxide (ns-$ZrO_2$) and, in particular, Ti oxide (ns-$TiO_2$), in the form of thin nanostructured films.

These oxide films are constituted by nanoparticles with a size distribution covering the range from about 2 to about 50 nm, centered within 5 and 15 nm, as observed with Transmission Electron Microscopy (TEM) and Atomic Force Microscopy (AFM).

Nanoparticles are randomly assembled to generate a porous structure with a mass density from about ½ to about 1/10, of the mass density of the corresponding bulk oxide, as measured by Quartz Crystal Microbalance (QCM) and AFM; in the case of ns-$TiO_2$, the mass density is typically about 1/7 of the mass density of dense $TiO_2$.

These materials are made up of both nanocrystalline and amorphous nanonoparticles as revealed by TEM and X-Ray Diffraction (XRD). In case of ns-$TiO_2$, it has been observed (Raman spectroscopy) that anatase and rutile phases coexist.

The films, when laid with a thickness of 50 nm, are transparent for wavelengths in the visible region.

In the particular case of ns-$TiO_2$, optical absorption becomes appreciable at about 320 nm, in UV region (UV-VIS spectroscopy). From absorption edge features, optical band gap (Tauc model) is evaluated between 3.2 to 3.6 eV. The refractive index of ns-$TiO_2$ has a value between 1.6 and 1.8, much lower than the one of bulk $TiO_2$ (2.5 in Anatase, 2.9 in Rutile), due to nanoscale porosity (Lorentz-Lorenz model).

The nanostructured films of the invention have a thickness comprised between 20 nm and 200 nm, preferably between 40 nm and 60 nm, with a surface roughness between 2 nm and 30 nm, preferably between 5 nm and 15 nm.

Thin films of these ns-$MO_x$ may be deposited over the support slide by several techniques, such as sputtering or Pulsed Laser Deposition (PLD); however, the preferred technique is through the use of a Pulsed Microplasma Cluster Source (PMCS). This technique allows the deposition of thin nanostructured films and it is based on the ablation of material from a cathode placed within the source through plasma generated by a flux of gas injected into the source chamber interfaced with a vacuum system. The pressure difference between the source and the vacuum chamber allows the extraction of the nanoparticulate. For a general reference to PMCS technique, see, for instance, European patent application EP 1031639 or the Journal of Physics D, 32 (1999), L105-109. PMCS is the preferred technique as it proved to guarantee the desired porosity characteristics on the deposited material.

When produced through PMCS, surface features of the ns-$MO_x$ films are consistent with the ballistic aggregation growth process, showing in particular a surface roughness depending on the thickness. For a thickness within 40-60 nm, surface roughness is between 5 nm and 15 nm, and typically between 8 nm and 12 nm (AFM).

The ns-$MO_x$ films are preferably treated after deposition with an oxygen plasma (treatment for 150 sec at 100 W), in order to increase wettability and improve capillarity in the microchannel, thus favouring spontaneous liquids flow inside the microchannel.

The preferred material for the functionalization of the slide is ns-$TiO_2$, stechiometric or not, preferably obtained by means of PMCS technique. Titanium dioxide is a highly biocompatible and bio-active material; in fact, said material proved not to interfere with normal cell activities, such as cell growth, nor to interact with reactants used in the preparation of cell cultures. In addition, nanostructured titanium dioxide shows a very low fluorescence background signal (autofluorescence), which improves the signal/noise ratio in the case of fluorescence-based measurements.

A nanostructured titanium dioxide coating is disclosed in WO 2007/009994 in the name of the Applicant. This document discloses substrates for immobilizing viruses or cells; this document however does not mention the use in the field of microfluidics, and does not hint to the fact that ns-$MO_x$ may have superior properties, compared to other known adhesion-promoting materials, when used in this specific field.

The part in which the groove is present may be a pad realized using different soft materials, generally polymers such as silicone or neoprene or PDMS (polydimethylsiloxane); or, it may be a thin slab of a stiff material, generally an inorganic material such as glass, quartz or the like.

The groove has typically a length in the order of millimeters and a cross-section with lateral dimensions in the order of tens or few hundreds of micrometers; holes and possible additional cavities also have dimensions below one millimeter. These features are typically produced by etching, that may be carried out with different techniques known in the art, such as powderblasting, chemical etching (e.g. HF etching), Deep Reactive Ion Etching or plasma etching, with the use or not of etching masks. In the case of polymeric pads other techniques, such as moulding or casting, may be used for forming the groove.

The groove may have different cross-section geometries, such as, for instance, squared, circular, hexagonal, etc.

according to the need; the most common cross-section is rectangular. It can also be composed of a variable number of microchannels, for instance.

Figures 1A, 1B, 1C:
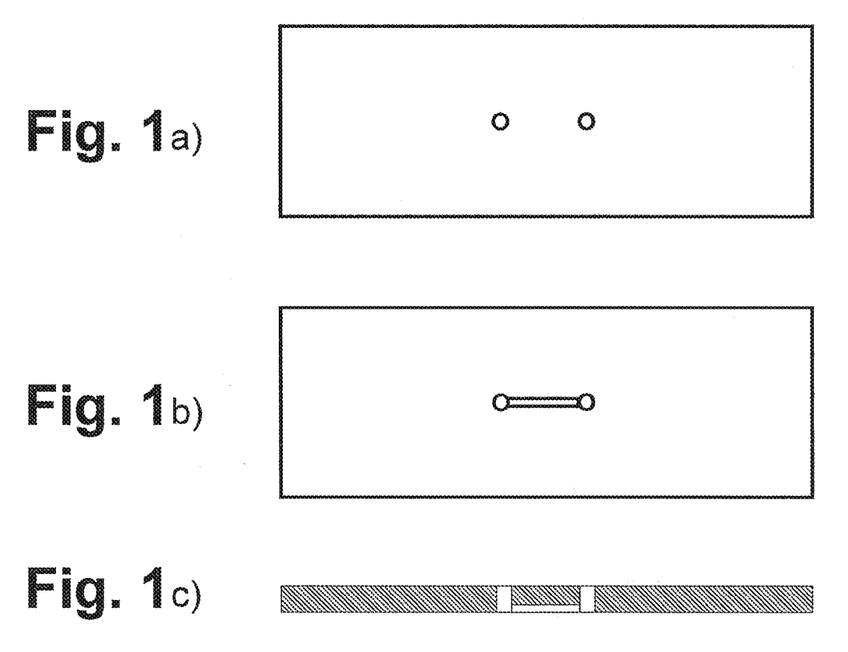
FIG. 1 shows the plane views and the section view of an exemplary microfluidic part.
Figure 2A:
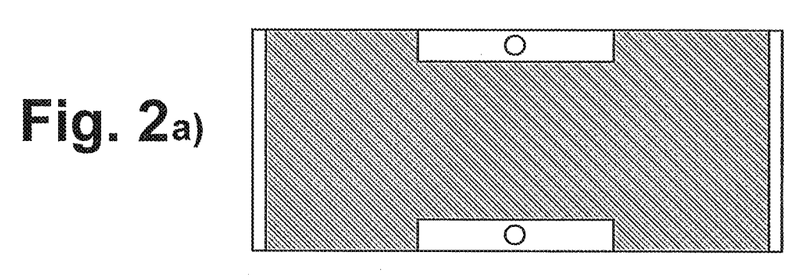
FIG. 2 shows an assembled device of the invention at different assembling stages.
Figure 2B:
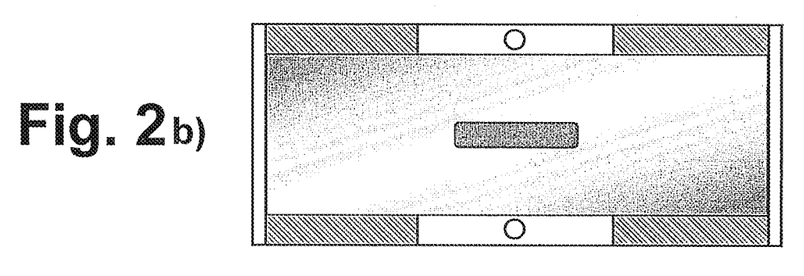
Figure 2C:
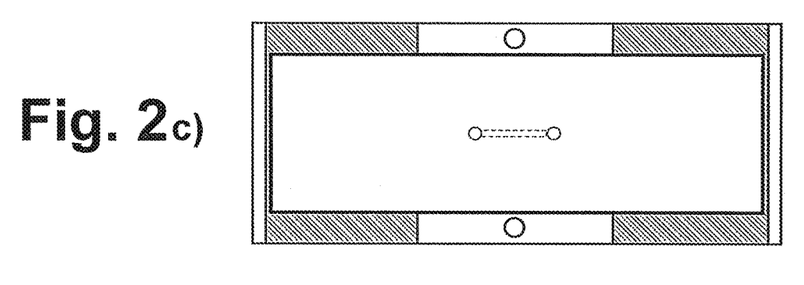
Figure 2D:
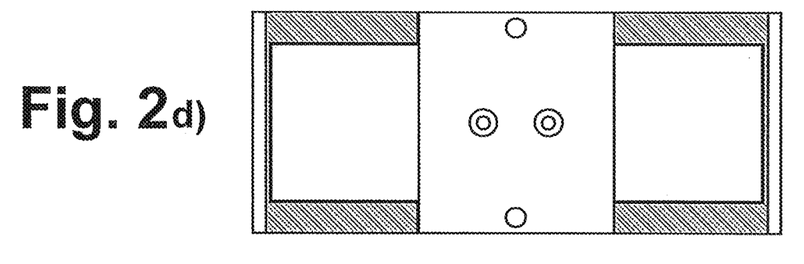

The preferred part with groove according to the invention is a polymeric pad. An example of pad with micrometric groove is represented in FIG. 1; in particular, in the figure, drawing a) shows the pad in top view, drawing b) shows the same pad in bottom view, and drawing c) shows a side view of the pad, in a cross section realized along a plane parallel to and including the groove.

Exemplary pad dimensions are 75.6×25.0×1.0 mm and exemplary groove dimensions are 300 μm×50 μm×10 mm; access apertures for reactants, gases and sample injection have a diameter of 0.7 mm.

The use of a microfluidic device in place of a plane slide, as in most state-of-the-art techniques, results in a low quantity of reactants needed to perform the assay. In particular, a much lower amount of expensive FISH probes will be required, which would be also environmentally safer.

In addition, in a microfluidic device according to the invention, the surface allowable for adhesion is of the same size of the bottom surface of the microchannel. This surface is much smaller than the functionally corresponding one in a standard FISH assay: if the coating for cell adhesion of the invention is provided, a similar amount of cells becomes available for analysis and this results in a minor amount of time to acquire the resulting images, thus reducing the costs due to machine-time allocation.

For the realization of miniaturized FISH, water-based (or water-compatible) reagents with different viscosity and density, must be sequentially used: since the reaction occurs in a microchannel, the capillarity of the microchannel is an essential pre-requisite for the flowing of reagents and the correct execution of the analysis. This condition can be obtained either by producing the pad or slab (in which the microchannel is obtained) with a hydrophylic material, or by functionalizing the substrate slide with a hydrophylic ns-$MO_x$ film.

In a preferred embodiment of the invention, a pad is used made of PDMS or silicone, which are known to be hydrophobic, preventing the spontaneous flowing of liquids inside the microchannel. Therefore it becomes necessary to post-treat the ns-$MO_x$ coatings, whenever the films as deposited are hydrophobic as well, in order to render these hydrophylic and thus favour the flowing of aqueous reactants inside the microchannel.

By post-treatment of ns-$MO_x$, preferably by surface charge adding (for instance by plasma oxygen treatment for 150 sec at 100 W), ns-$MO_x$ coatings with high wettability are obtained, as measured by contact angle analysis (contact angles not above 10° have been consistently obtained by the inventors of in the case of plasma treated coatings). The inventors have observed that such treatment is able to confer capillarity in the context of microchannels, and verified that liquids flow inside the microchannel spontaneously, with no need of pump assisted aspiration, confirming the capillarity of the device.

The first, simplest embodiment of the microfluidic device of the invention, comprises a functionalized microscope glass slide which is coupled with a PDMS or silicone pad provided with a micrometric groove. The coupling may exploit at least partially the spontaneous adhesion between PDMS or silicone and glass. This adhesion is however reversible, allowing an easy separation of the two parts at the end of the assay.

The assembling will be performed so that the microchannel is located in correspondence to the functionalized area on the surface of the slide. Thanks to the reversible coupling between slide and pad, this latter can be removed at the end of the hybridization phase so that the fluorescence images may be directly acquired on the glass slide without any further manipulation of the sample being necessary.

Unexpectedly, it has been observed that said first coupling and said later detaching steps do not affect to any extent the adhesion of the cells onto the functionalized layer of the slide neither before nor after the FISH assay is performed.

Once uncoupled, the slide can thus be directly placed "under" a microscope, with the microscope objective facing the slide side on which the sample is fixed. This allows to correctly set the working distance, permitting image acquisition with a 100× objective, thus getting to the image resolution required by FISH usual-practice standards.

At the same time, the possibility to use, for instance, a 1 mm thick standard microscope glass slide allows to obtain a device robust enough to be handled easily.

As above disclosed, FIG. 2 represents a top view of an assembled device of the invention at different assembling stages. In the Figure, drawing a) represents a support; drawing b) is the support with the functionalized slide, in which the central area represented in a darker shade is the functionalized area; drawing c) is the support with the functionalized slide and the microfluidic pad laid onto the latter; drawing d) is the final assembled device with closure provided with access ports to the microfluidics.

Due to spontaneous adhesion between PDMS or silicone and glass, the described assembly could be unnecessary if a microfluidic pad made of one of these polymers is used. Nevertheless, it is necessary to provide compression between parts if such polymers are not used, in particularly regarding further possible embodiments of the invention, such as the ones described below and named "Gasket 1", "Gasket 2" and "Gasket 3".

Figure 3A:
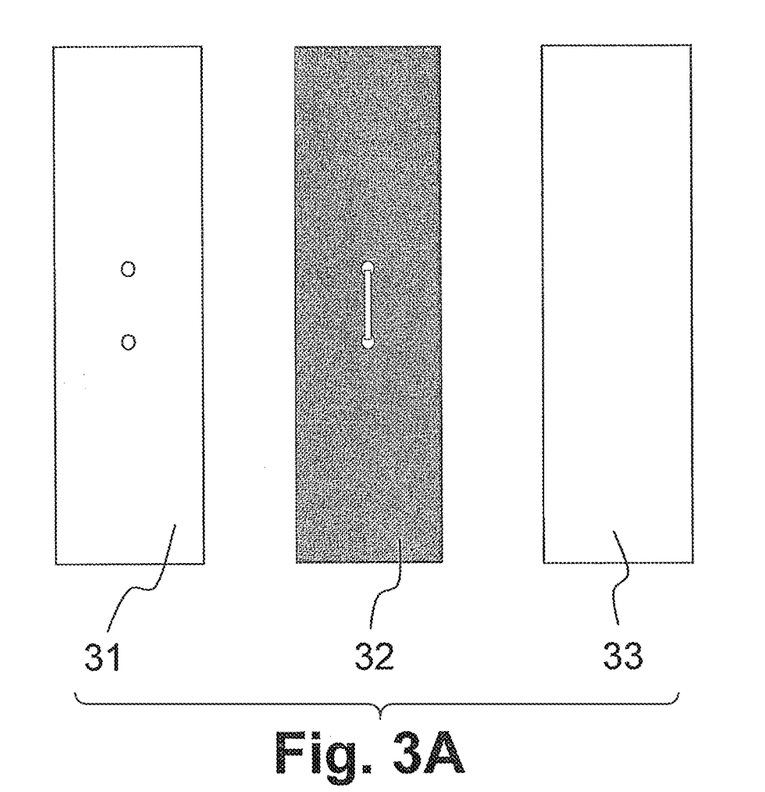
FIG. 3A shows the parts making up a device of the invention in a first embodiment thereof.
Figure 3B:
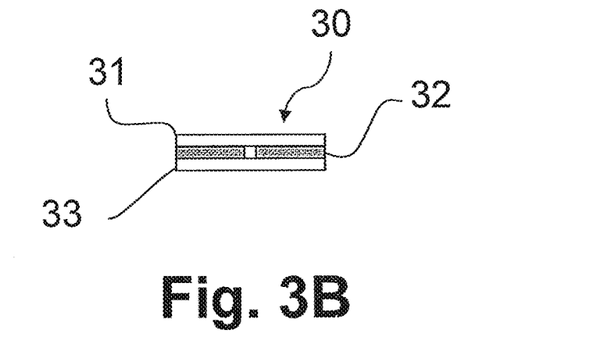
FIG. 3B shows a section view of the assembled device of FIG. 3A.

The embodiment "Gasket 1" is represented in FIGS. 3A and 3B. FIG. 3A shows the three elements making up a microfluidic device according to this first embodiment, namely an upper slide, 31, provided with microfluidic access apertures for reactants, and sample injection (that may be realized with any suitable organic or inorganic stiff material, e.g. glass); the pad 32 in which an opening is produced; and part 33 is the functionalized slide. FIG. 3B shows a cross section of the device 30 obtained by joining the elements 31, 32 and 33 of FIG. 3A, said cross section taken along a plane perpendicular to the flow direction of fluids in the microchannel of the device. With the construction of FIG. 3B, the assembly of slide 31 and pad 32 defines the groove, and slide 31 may be slightly compressed against pad 32, that thus acts as a gasket, ensuring a liquid tight seal to the device. Said pad 32, in particular, may be realised in polymeric material, such as, for instance, PDMS, silicone or neoprene.

The assembling of the device is performed so that the functionalized area of slide 33 is put in correspondence to the opening in pad 32.

Figure 4A:
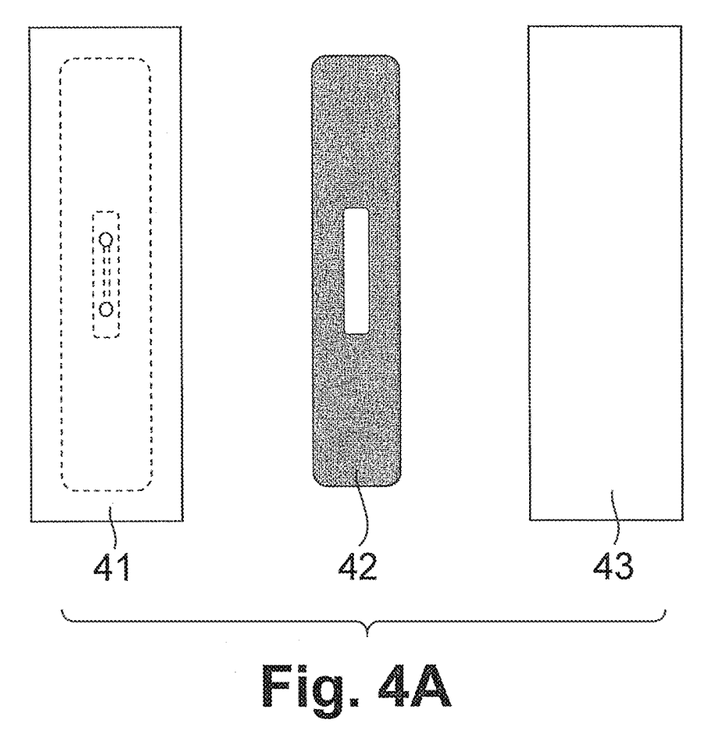
FIG. 4A shows the parts making up a device of the invention in a second embodiment thereof.
Figure 4B:
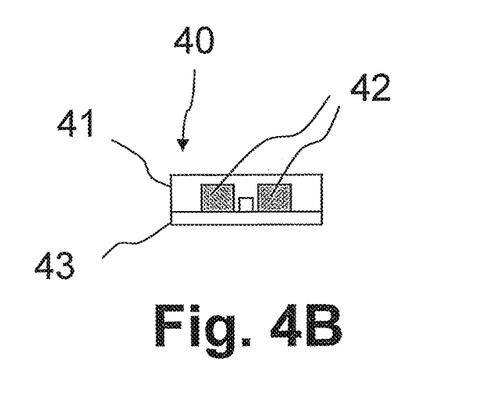
FIG. 4B shows a section view of the assembled device of FIG. 4A.

FIGS. 4A and 4B show a further particular embodiment, named "Gasket 2" (device 40 in FIG. 4B), of the microfluidic device of the invention; the relation between the views in FIG. 4A and FIG. 4B is the same as in FIGS. 3A and 3B. In this case the microchannel is realized in a slide 41 in FIG. 4A.

In this embodiment, the functionalised slide 43 is coupled to the slide 41 provided with groove and openings for access to the microchannel. In order to allow a liquid tight seal between slides 41 and 43, a seal 42 is present between them. Said seal, in particular, may be realised in polymeric material, such as, for instance, PDMS, silicone or neoprene. Said seal 42 is provided with a suitable aperture in order not to cover the functionalized area of the slide 43 in FIG. 4A.

The assembling is performed so that the microchannels of the slide 41 are put in correspondence to the functionalized area of the slide 43.

Figure 5A:
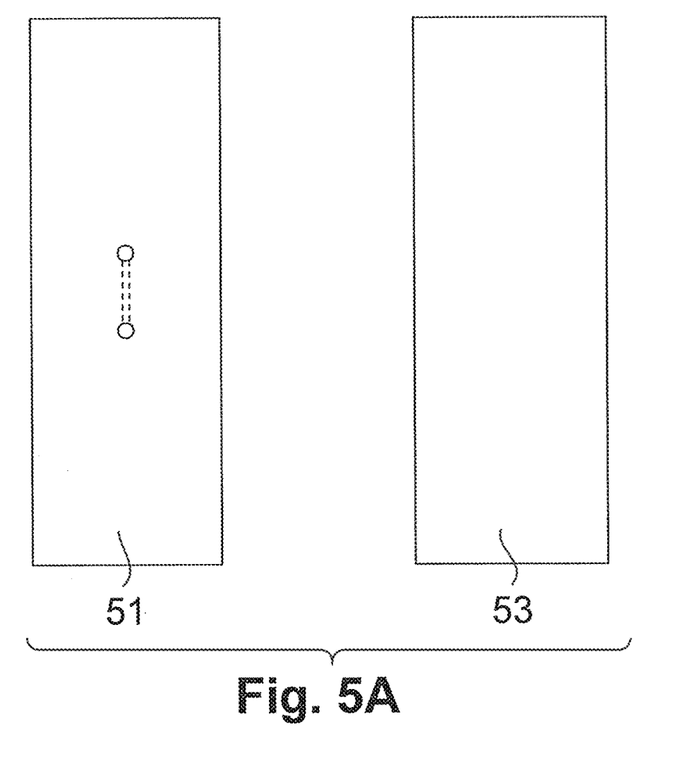
FIG. 5A shows the parts making up a device of the invention in a third embodiment thereof.
Figure 5B:
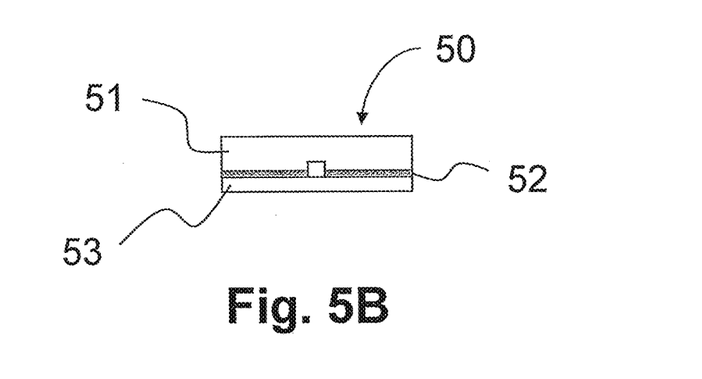
FIG. 5B shows a section view of the assembled device of FIG. 5A.

FIGS. 5A and 5B show a still further embodiment, named "Gasket 3" of the device of the invention (device 50 in FIG. 5B); again, the relation between the views in FIG. 5A and FIG. 5B is the same as in FIGS. 3A and 3B. In this embodiment, the device is formed of a first slide 51 and the functionalized slide 53 shown in FIG. 5A; slide 51 is provided with the groove and apertures for reactants, gases and sample injection. The liquid tight seal between slides 51 and 53 is allowed by a thin polymeric layer (52, not shown in FIG. 5A), preferably few micrometers thick, definitely attached to the slide 51, which does not cover the part of this slide provided with the groove.

All the slides used in the above embodiments may be any suitable slides, such as, for instance, glass slides like microscope glass slides.

The device of the invention in all the embodiments unexpectedly proved to solve major problems of the technologies disclosed in the prior art.

In fact, the adhesion of the cells to the functionalized substrate proved to be of 90% or more of the initial cells, which is surprising with respect to the state-of-the-art. Unexpectedly, these adhesion percentages have also been obtained when dealing with haematopoietic cells, such as U937, which are lymphoma derived cells, commonly defined as non-adhering cells. As a consequence, even samples with a low number of cells may be used, with a reasonable expectation of reproducibility and acquisition of enough information.

This is of a great concern, especially when large samples cannot be dealt with, such as, for instance, with samples of Circulating Tumor Cells.

Again, the identification of rare cell alterations would be equally possible due to the very limited loss of cells from the sample during the processing, thus reducing the risk of false negatives.

Moreover, since the cells adhered to the slide maintain their 3D configuration, instead of being spread and pressed on the slide as in traditional practices, three-dimensional (3D) images may be obtained by collecting data at different distances from the sample. This advantage also is of great concern when dealing with rare cell alterations or with low cell number samples, allowing to discriminate signals on the z axis too, thus permitting not to reject potentially interesting information for geometrical problems.

As a second object of the present invention, it is provided a method for using the device of the invention in analytical fluorescence based assays and, in particular, for performing FISH.

For the purposes of this invention, in particular, a cell suspension constituted by cells from biological samples, cultured in vitro, extracted from tissues or from fluids may be used.

A tailored protocol has been implemented, allowing to obtain unexpected and surprising effects with respect to any other prior method and/or materials used.

In fact, the method allows to analyze even small size and low density samples, with concentration as low as around 10 cells/ml.

More in detail, the assay may be performed on different types of cells, such as for instance tumor cells, circulating tumor cell, hematopoietic cells, epithelial cells, amniocytes and in general any cultured or primary mammalian and not mammalian type of cells, either living or previously fixed with any suitable cell fixative, being commonly classified as adhering or non-adhering cells as above said. Living or fixed, adhering or non-adhering cells may be immobilized to the functionalized slide at a very different extent.

In a preferred embodiment, the analytical fluorescence based assays of the invention is performed on living U937 cells, which are commonly defined as non-adhering cells.

By allowing the use of a living cell suspension, the method of the invention does not require any previous treatments of the cells with fixing agents, nor lysis of cell, thus permitting the use of integral cells. This is of particular concern, in terms of time, cost and volume of toxic reagents; in addition, analysis of the physiological conditions of the cells may thus be performed.

The method disclosed in the present invention is particularly suitable to be performed using the device of the invention.

The invention will be further illustrated by the following examples.

Example 1

This example is about the preparation and assembling of microfluidic devices with a microchannel according to the invention.

a) Functionalization of the Base Slide with a ns-$MO_x$

A ultrasonically cleaned microscope glass slide (for example Schott Nexterion D) is put into the deposition chamber of a vacuum system equipped with a PMCS. The exposition of the slide to the cluster beam generated by PMCS takes place through a suitable stencil mask, which is positioned between the source and the slide, in order to allow the deposition of the desired material only on limited areas of the slide. To obtain a uniform thickness of the deposited layer, the slide is continuously rastered in front of the cluster beam; to monitor the thickness of the growing layer a quartz crystal microbalance (QCM) is exposed to the cluster beam too. Deposition is performed at room temperature, at a typical pressure of $10^{-6}$ torr, and lasts around 1 min per slide, provided a source-slide distance around 1 m. The chosen material for functionalization of the slide is $TiO_2$.

The resulting ns-$TiO_2$ film has an average thickness of about 50 nm.

After the deposition phase, the slide is exposed to a oxygen plasma for 150 sec at 100 W.

b) Coupling of the Groove with the Slide

A PDMS pad of the kind shown in FIG. 1 is provided, in which is present a micrometric groove of length 1 cm, width 300 μm and height 50 μm. The pad and the functionalized slide are coupled using a suitable mechanical centerer, providing the positioning of the groove onto the functionalized area of the slide, thus forming a microchannel according to the invention.

Adhesion between the two parts is obtained by exerting a slight pressure.

Example 2

Comparative

A microfluidic device is produced by joining a PDMS pad equal to the one used in Example 1 with a non-functionalized microscope glass slide; in this case too adhesion between the pad and the slide is obtained by simply applying a slight pressure to the two parts.

Example 3

Comparative

The procedure of Example 2 is repeated, using in this case a slide functionalized with a layer of dense, non-nanostructured TiO₂ film obtained through a standard sputtering deposition method; the resulting film has a thickness of about 50 nm. In this case too adhesion between the slide and the pad is obtained by pressing the two parts.

Example 4

Comparative

The procedure of Example 2 is repeated, using in this case a slide functionalized with a layer of poly-D-lysine by incubating a glass slide with a solution of 15 µg/ml of poly-D-lysine (SIGMA) for 30 min at room temperature, then washing in 1× Dulbecco's Phosphate Buffered Saline (DPBS), air drying and using for the experiment; in this case too adhesion between the slide and the pad is obtained by pressing the two parts.

Example 5

This example illustrates the results of a cell adhesion test carried out on the microfluidic devices of Examples 1-4.

The microfluidic devices are pre-incubated a 37° C. on top of a hot plate for a period of 2 min.

For the preparation of the test specimens, cultured U937 cells (1 ml of exponentially growing cells) are placed in 1.5 ml tube and washed 3 times with 1×DPBS, counted and finally resuspended at the concentration of 10000 cells/µl.

Figure 6:
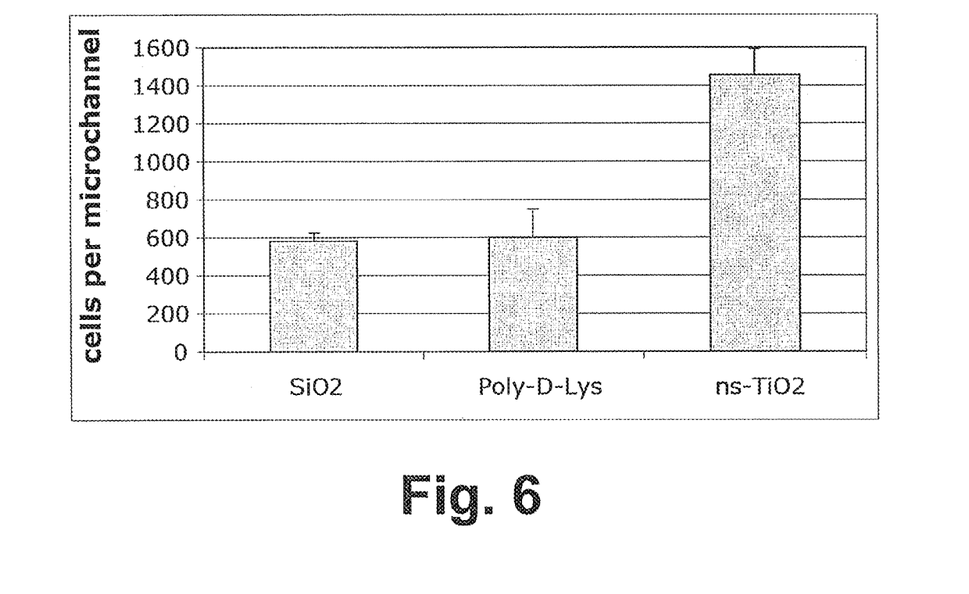
FIG. 6 schematically shows the results of tests of adhesion of cultured cells (U937) onto a functionalized slide according to the invention, and onto slides not of the invention.

1.5 µl of cell suspension are loaded into the inlet well of the microchannel of each microfluidic device, while aspirating from the outlet well of the microchannel with a syringe pump (KDS120, KD Scientific) at 1.7 µl/s; the cells are then left to adhere to the bottom of the microchannel for few mins and immediately fixed by adding a solution of methanol/acetic acid 3:1 ratio. After adhesion, 1×DPBS is added to wash the fixative while aspirating with a vacuum pump; this procedure subjects cells to limited shear stress. At the end of the procedure, the pad is removed, the slides are stained with DAPI (4,6-Diamidino-2-phenylindole, SIGMA), and mounted for microscopy analysis. In the analysis, the number of cells fixed onto the slide are counted. The results are reported in FIG. 6: as it is clearly seen from this figure, in the test conditions the number of U937 cells adhered onto the surfaces of the slides of Comparative Examples 2-4 is similar, and equal to about 600 fixed cells, namely, about 40% of the loaded cells; on the other hand the number of cells adhered onto the functionalized slide of the invention (Example 1) is about 1400, that is, about 130% higher than in the case of comparative slides, and equal to approximately 93% of the loaded cells.

Example 6

This example illustrates the results of a second cell adhesion test carried out on the microfluidic devices of Examples 1-4, under more severe shear stress conditions than in Example 5.

The procedure of Example 5 is repeated up to the fixation step with the 3:1 methanol/acetic acid solution; the samples are then subjected to a procedure, called in the following "prolonged shear stress", comprising contacting the cells fixed onto slides with a series of reagents used in biological assays. In particular, the following solutions are sequentially loaded with a pipet, incubated for the indicated time and temperature and aspirated with vacuum pump: 2× saline-sodium citrate buffer (SSC) for 30 min at 37° C., buffer with enzyme (0.005% pepsin, 0.01 N HCl, SIGMA) for 15 min at 37° C., 1×DPBS for 5 min at room temperature (RT), post fixative (50 mM MgCl₂, SIGMA), 0.95% formaldehyde (SIGMA) in 1×DPBS for 5 min at RT, 1×DPBS for 5 min at RT, three subsequent washings with EtOH 70%, 85% and 100% (BDH) for 1 min each at RT, denaturing solution (70% formamide, SIGMA, in 2×SSC SIGMA) for 5 min at 75° C., three subsequent washings with EtOH 70%, 85% and 100% for 1 min each at RT.

After complete aspiration of pure EtOH, the slides are placed at 60° C. for 2 min to dry completely, and then loaded with 0.3 µl of the hybridization mix (for 15 ml: 7.5 ml ultrapure formamide, 6.0 ml dextran sulfate 25%, 1.5 ml 20×SSC). Microchannel wells are then sealed with a drop of mineral oil (SIGMA) to prevent evaporation, and incubated for 10 min at 37° C. After incubation, pads are removed and slides are dipped in coplin jars containing wash solution A (0.3 NP40, nonionic, non-denaturing detergent octyl phenoxylpolyethoxyethanol, in 0.4×SSC (SIGMA)) for 2 min at 73° C., and wash solution B (0.1% NP40 in 2×SSC) for 1 min at RT, air dried and mounted with DAPI II (Abbott Molecular) for microscopy analysis. For cell counting, each slide is imaged with DAPI filter and acquired with Scan^R, a microscope-based automated platform for imaging screening (Olympus Europa, Germany) equipped with a Hamamatsu ORCA-AG camera, by scanning 13 adjacent images using 10× objective; then cells are counted using ImageJ software "analyze particles" function after having set a proper threshold and excluding objects outside the range of 15-75 square pixels. Data are exported and analyzed by Excel software.

Figure 7:
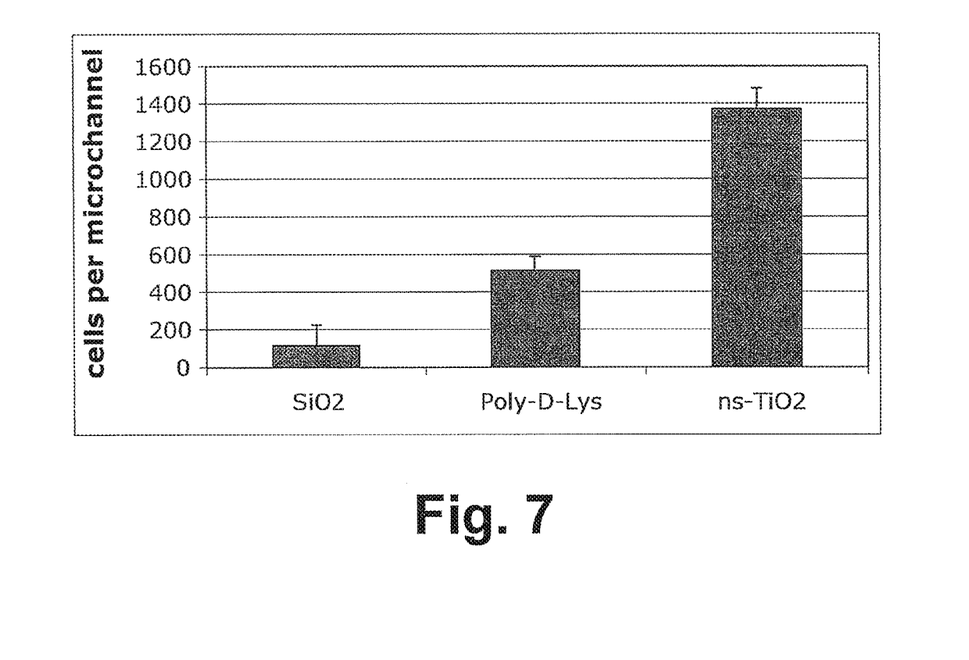
FIG. 7 schematically shows the results of tests of adhesion of cultured cells (U937) onto a functionalized slide according to the invention, and onto slides not of the invention, after a complete microfluidic run (prolonged shear stress procedure)

The results are reported in graphical form in FIG. 7. As can be seen from the figure, on the SiO₂ slide the cell number decreased dramatically down to ~100 cells/microchannel, while was substantially unchanged on ns-TiO₂ and poly-D-lysine coated slides. Nevertheless, due to different efficiency of initial cell immobilization (see Example 5), at the end of the prolonged shear stress test, the total cell number was significantly different between ns-TiO₂ and poly-D-lysine (1400 cells versus 600 cells) being more that two fold higher on ns-TiO₂ coated slide.

Example 7

This example illustrates the results of a third cell adhesion test carried out on the microfluidic devices of Examples 1-4, carried out under the same conditions of Example 6, in this case with specimen comprising hematopoietic cells from a human donor.

The microfluidic devices are pre-conditioned a 37° C. on top of a hot plate for a period of 2 min as in Example 5.

For the preparation of the test specimens, an aliquot of Peripheral Blood (PB) (0.5-1 ml) of normal donor is treated with Red Blood Lysis (RBL) buffer (0.15 M NH₄Cl, 9.93 mM KHCO₃, 0.13 mM EDTA, from SIGMA) to an overall volume of 10 ml; the suspension is kept at 4° C. for 5 min, then centrifuged at 1500 rpm for 5 min. Supernatant is discarded and the thus isolated hematopoietic cells are resuspended again in 10 ml of RBL buffer, then centrifuged at 1800 rpm for 5 min.

The cells are resuspended in 1 ml of 1×DPBS and transferred in 1.5 ml tube, washed twice in 1×DPBS, and finally resuspended at a concentration of 15000-25000 cells/µl. 1.5 µl of the thus-obtained suspension are loaded into the inlet well of the microchannel of each microfluidic device.

Figure 8A:
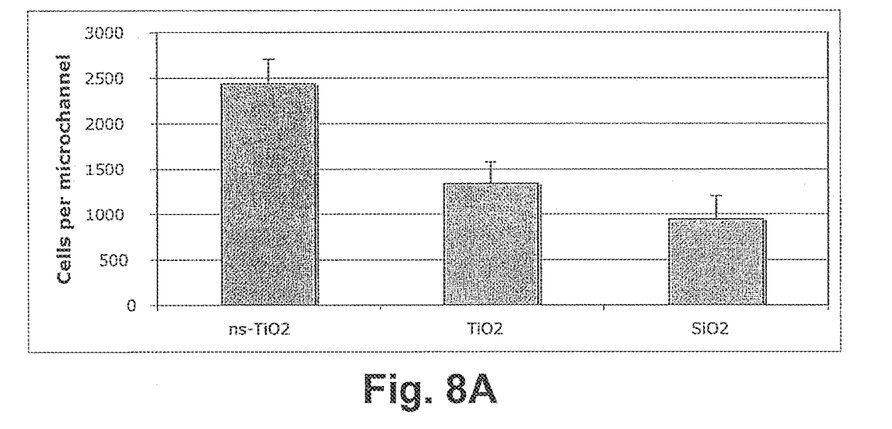
FIGS. 8A, 8B and 8C schematically show the results of tests of adhesion of primary hematopoietic cells onto slides functionalized with different nanostructured metal oxides according to the invention, and onto slides and metal oxides not of the invention.
Figure 8B:
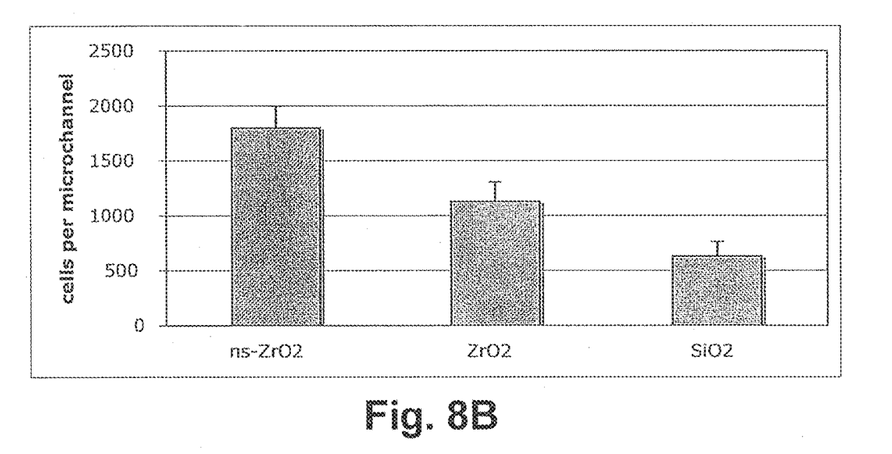
Figure 8C:
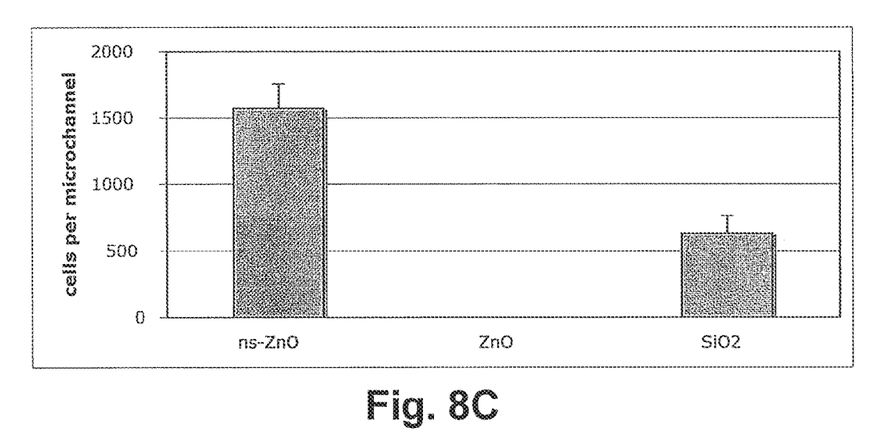

20 µl of Carnoy's fixative Methanol (SIGMA)/Acetic acid (Carlo Erba) 3:1 are added on the inlet well and left to diffuse into the to fix cells. After 2 min cells are fixed. The microchannels are then subjected to the prolonged shear stress procedure illustrated in Example 6. The results of the test are represented in FIG. 8: the number of cells retained onto the device of the invention ranges between about 1.8 and 2.5 times the number of cells retained onto comparison devices.

Example 8

This example is about the comparison of performance of devices of the invention in which the ns-TiO$_2$ film is post-treated or not after deposition.

The functionalized face of a slide produced as described in point a) of Example 1 is subjected to a plasma oxygen treatment during 150 seconds at 100 W.

Figure 9:
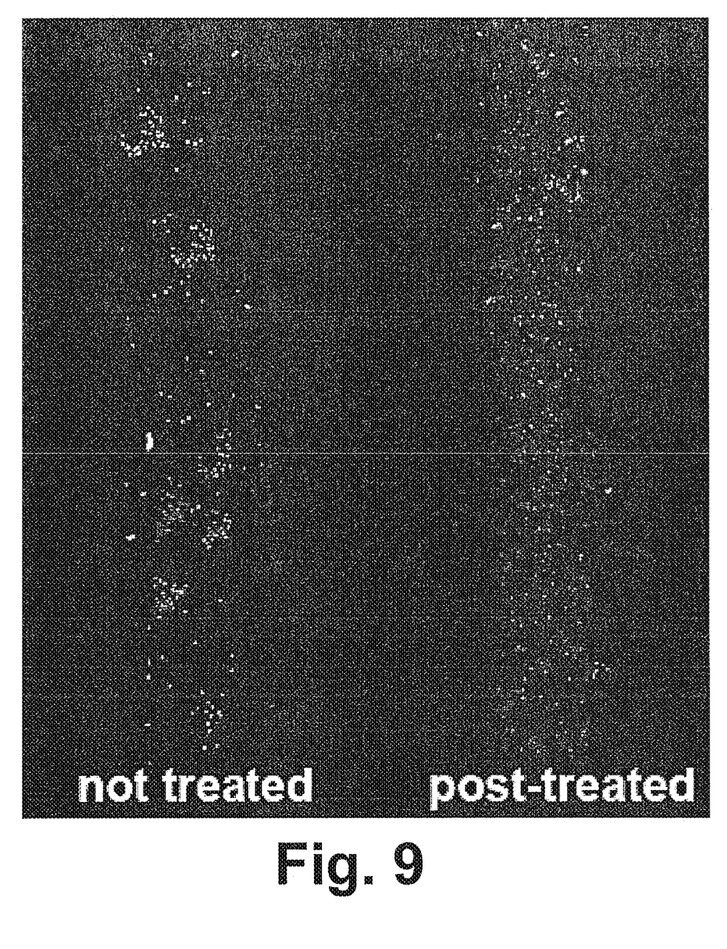
FIG. 9 shows the result of adhesion test on two devices of the invention.

The thus post-treated slide, and a non post-treated slide, are assembled with PDMS pads as in Example 1, and then subjected to the procedure of Example 6, using in this case fixed cells (U937) as test sample. The results of the test are reported in FIG. 9, and show that both devices of the invention present high retention of cells, but in the case of the post-treated ns-TiO$_2$ film these are more evenly distributed over the surface corresponding to the bottom of the microchannel. This favours the data interpretation.

Example 9

This example is about the realization of a complete FISH assay protocol using a microfluidic device of the invention.

A microfluidic device prepared according to Example 1 is used for performing a FISH assay according to the protocol of the invention.

An aliquot of U937 cells (ATCC American Type Culture Collection) is centrifuged at 600 g for 5 min and suspended in 1×DPBS at 37° C. up to a cell concentration of 10000 cells/µl.

The cell suspension is manually pipetted into the device using a standard laboratory pipet and is left incubating for 4 min.

An immobilizing agent comprising an alcohol and a weak carboxylic acid is added (methanol/acetic acid 3:1) and immobilization is allowed to occur for 2 min; then, aspiration with a vacuum pump is performed.

30 µl of 2×SSC solution (prepared from a concentrated stock of 20×SSC, 3.0 M NaCl, 0.3 M sodium citrate) pre-heated at 37° C. is pipetted into the microchannel and incubation is allowed to happen for 15 min on a plate heated at 37° C.

After incubation, a solution containing pepsin 0.005% is pipetted and then incubated into the microchannel for 15 min on a heated plate.

The pepsin solution is pumped out, 1×DPBS (Phosphate Buffer Saline, Lonza Group) is pipetted, left incubating for 5 min, then a solution containing formaldehyde (for 50 ml of solution: 1.3 ml formaldehyde 37%, 0.23 g MgCl$_2$, 48.7 ml PBS) is incubated for 5 min, fluxed with 1×DPBS and left incubating for 5 min. DPBS is pumped out from the microchannel, which is left drying.

A series of 70%, 85% then 100% ethanol solutions is sequentially pipetted and each one incubated for 1 min.

A denaturing solution (for 50 ml of solution: 35 ml formaldehyde 37%, 5 ml of 20×SSC, 10 ml H$_2$O at pH 7-8) pre-heated at 73° C. is pipetted, allowing incubation for 5 min on a plate heated at 73° C.

The device is then removed from the plate and left cooling, after which the denaturing solution is pumped out and the treatment with ethanol solutions is repeated.

The device is placed on a plate heated at 45° C. and ethanol is completely removed by pumping out for about 1 min.

The device is removed from the heating plate and a denatured probe labeled with Cy3 is loaded. The microchannel is then sealed with a drop of mineral oil (Sigma) and incubation is allowed overnight on a plate kept at 37° C.

After incubation the pad is separated from the slide: the glass slide is then washed for 2 min in a coplin jar with a solution containing 0.4×SSC and 0.3% NP40, pre-heated at 73° C.; then for 1 min with a solution containing 2×SSC and 0.1% NP40 at RT. At the end the slide is allowed to dry in air for 1 min.

A glass cover slide is then applied with a solution containing DAPI (4,6-Diamidino-2-phenylindole, SIGMA).

Figure 10:
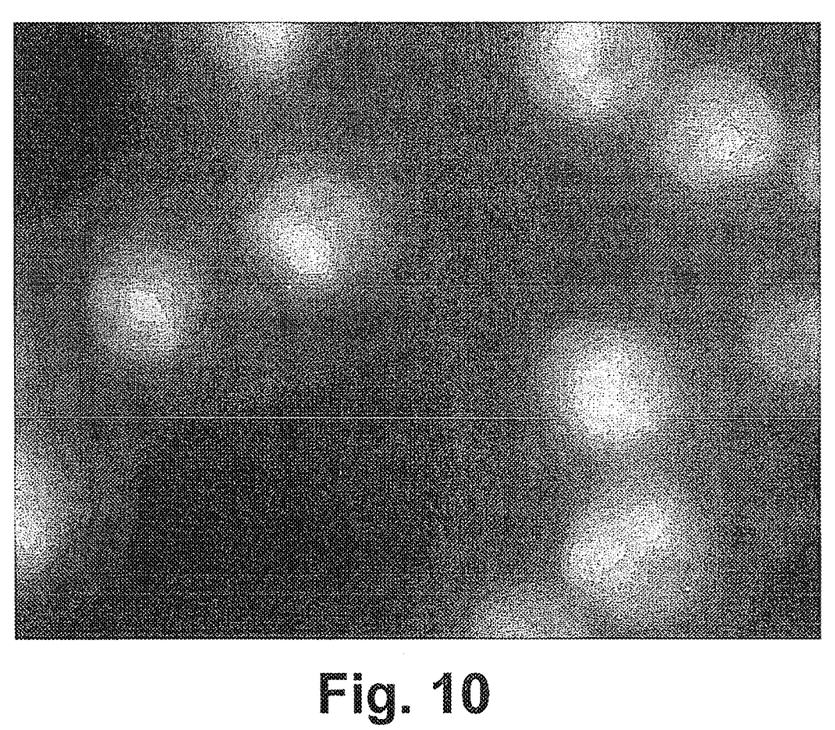
FIGS. 10 and 11 show cultured cells (U937) after FISH tests in microchannel using devices of the invention.
Figure 11:
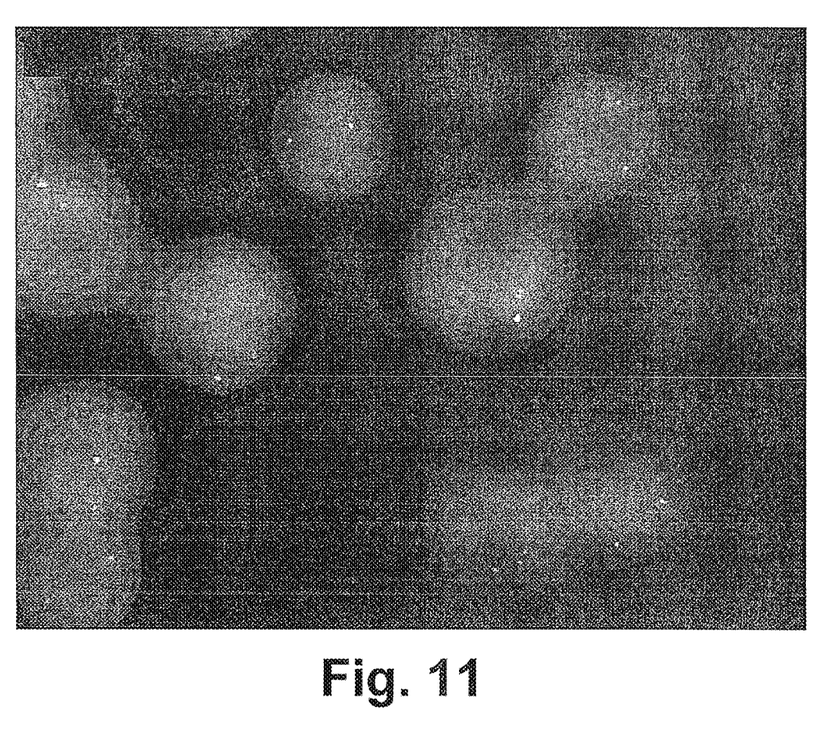

The slide is thus ready to be used for acquiring images with an oil immersion 100× objective (see FIG. 10 and FIG. 11).

FIG. 10 shows the precise detection on cell nuclei of chromosome X by Cy3 labelled Locus Specific probe (see two bright dots/nucleus), by FISH, confirming the effective performance of the test, even using low abundance sequence probes for the genomic detection.

FIG. 11 shows the precise detection on cell nuclei of chromosome X by Cy3 labelled Centromere Specific probe (see two bright dots/nucleus), by FISH, further confirming the optimal performance of the test.

While the present invention has been illustrated and described with respect to a particular embodiment thereof, it should be appreciated by those of ordinary skill in the art that various modifications to this invention may be made without departing from the spirit and scope of the present.

What is claimed is:

1. A microfluidic device for visual analysis of immobilized cells comprising a slide and a part in which at least one groove is present, said part being a pad of silicone and being reversibly coupled to the slide due to spontaneous adhesion between said pad and said slide, said slide and said part being such that their joining defines a microchannel, said microchannel being accessible from a top surface of the device via through holes present in said part, wherein at least the area on a surface of said slide facing said microchannel is functionalized with a hydrophilic nanostructured metal oxide film of thickness comprised between 20 nm and 200 nm with a wettability contact angle lower than 10°, wherein the nanostructured metal oxide film has a porous structure with a mass density from about ½ to about 1/10 of the mass density of the bulk oxide corresponding to the nanostructured metal oxide film.

2. The microfluidic device of claim 1, wherein said nanostructured metal oxide is constituted by nanoparticles with a size distribution covering the range from about 2 to about 50 nm and centered within 5 and 15 nm.

3. The microfluidic device of claim 1, in which said oxide is selected among Ti oxide, Zn oxide or Zr oxide.

4. The microfluidic device of claim 1, wherein said film has a thickness comprised between 40 nm and 60 nm and a surface roughness comprised between 5 and 15 nm.

5. The microfluidic device of claim 1 wherein the oxide is Ti oxide with mass density about 1/7 of the mass density of dense TiO2, optical band gap between 3.2 and 3.6 eV and refractive index between 1.6 and 1.8.

6. The microfluidic device of claim 1 wherein said film is deposited by pulse microplasma cluster source technique.

7. A microfluidic device for visual analysis of immobilized cells comprising a slide and a part in which at least one groove is present, said part being a pad of soft material reversibly coupled to the slide due to spontaneous adhesion between said pad and said slide, said slide and said part being such that their joining defines a microchannel, said microchannel accessible from a top surface of the device via through holes present in said part, wherein on a surface of said slide facing said microchannel at least an area facing said microchannel is functionalized with a hydrophilic nanostructured metal oxide film of thickness comprised between 20 nm and 200 nm with a wettability contact angle lower than 10°, wherein said oxide is plasma-treated to obtain and retain said wettability contact angle lower than 10°, wherein the nanostructured metal oxide film has a porous structure with a mass density from about ½ to about 1/10 of the mass density of the bulk oxide corresponding to the nanostructured metal oxide film.

8. The microfluidic device of claim 7 wherein the plasma treatment is oxygen plasma treatment for about 150 seconds at about 100 watts.

9. An analytical fluorescence based assay in which is used the microfluidic device of claim 1.

10. The analytical fluorescence based assay of claim 9 in which said assay is a FISH assay.

11. The analytical fluorescence based assay of claim 10, in which said FISH assay is carried out according to a protocol comprising the steps of:
  a) loading a cell sample into the microchannel of the microfluidic device of claim 1;
  b) leaving the cells incubating;
  c) fixing the cells with a solution of an alcohol and a weak carboxylic acid;
  d) fluxing with SSC;
  e) fluxing with a solution of pepsin;
  f) post-fixing with a solution of formaldehyde;
  g) adding a series of solutions of ethanol;
  h) adding a solution of a denaturing agent;
  i) repeating step g) once;
  j) adding the labelled probe and leaving incubating;
  k) removing the part hosting the microchannel from the slide; and
  l) washing with a solution comprising SSC and NP40,
wherein the cell sample is in the form of a cell suspension.

12. The analytical fluorescence based assay of claim 11, wherein said cell suspension is a suspension of non-adhering cells.

13. The analytical fluorescence based assay of claim 12, wherein said non-adhering cells are living cells.

14. The analytical fluorescence based assay claim 13 wherein said cells are fixed cells.

* * * * *